United States Patent
Purdy et al.

[11] Patent Number: 5,460,177
[45] Date of Patent: Oct. 24, 1995

[54] METHOD FOR NON-INVASIVE MEASUREMENT OF CONCENTRATION OF ANALYTES IN BLOOD USING CONTINUOUS SPECTRUM RADIATION

[75] Inventors: David L. Purdy, Marion Center; Perry Palumbo, New Kingston; Mark DiFrancesco, Indiana, all of Pa.

[73] Assignee: Diasense, Inc., Indiana, Pa.

[21] Appl. No.: 59,162

[22] Filed: May 7, 1993

[51] Int. Cl.$^6$ .................................................. A61B 5/00
[52] U.S. Cl. ................................................ 128/633; 356/39
[58] Field of Search .................................. 128/633–634, 128/664–667; 356/39–41

[56] References Cited

U.S. PATENT DOCUMENTS

| | | | |
|---|---|---|---|
| 4,948,248 | 8/1990 | Lehman | 128/633 X |
| 5,119,815 | 6/1992 | Chance | 128/665 X |
| 5,187,672 | 2/1993 | Chance et al. | 128/633 X |
| 5,213,105 | 5/1993 | Gratton et al. | 128/665 X |
| 5,303,026 | 4/1994 | Strobl et al. | 128/665 X |

*Primary Examiner*—Angela D. Sykes
*Attorney, Agent, or Firm*—Webb Ziesenheim Bruening Logsdon Orkin & Hanson

[57] ABSTRACT

Method for non-invasive detection of the concentration of a constituent in blood of a living animal includes the steps of irradiating a body part of the animal with intensity-modulated radiation over a continuous spectrum; determining the intensity of radiation emitted from the body part at wavelength ranges within the continuous spectrum; and using the determined intensity to calculate the concentration of the constituent. A radiation source including a radiating bulb and a chopper for periodically interrupting radiation emitted from the bulb may be provided.

13 Claims, 1 Drawing Sheet

METHOD FOR NON-INVASIVE MEASUREMENT OF CONCENTRATION OF ANALYTES IN BLOOD USING CONTINUOUS SPECTRUM RADIATION

BACKGROUND OF THE INVENTION

This invention relates to techniques for non-invasively detecting the concentration of analytes in the blood of living animals, and in particular to the use of continuous spectrum infrared spectroscopic techniques for the non-invasive detection of glucose concentrations in the blood of humans.

In the diagnosis and treatment of various conditions, it is important to measure the concentration of various constituents in the blood. For example, in the treatment of diabetes, the concentration of glucose in the blood must be measured on a periodic basis. For persons experiencing insulin-dependent or Type I diabetes, it is often necessary or desirable to measure blood glucose concentrations several times each day. Obtaining accurate readings of cholesterol concentrations is important in the prevention of coronary artery disease. The measurement of the concentration of other blood analytes, such as bilirubin and alcohol, is also important for various diagnostic purposes.

The accurate measurement of concentrations of such blood constituents, as it is now practiced, requires obtaining a blood sample, such as by pricking a finger. The obtaining of blood samples by invasive techniques, such as pricking the finger, is both painful and inconvenient. In the case of diabetics, the need to lance a finger several times a day to monitor glucose levels result in a buildup of scar tissue. Indeed, many diabetics are believed not to monitor their glucose levels as frequently as recommended because of the pain and inconvenience of the invasive method. The result of such a failure to monitor glucose levels is a greater risk of experiencing the long-term health effects of diabetes. These health effects include damage to the eyes, resulting in partial and often total loss of vision, as well as other serious health problems. Millions of individuals in the United States alone suffer from diabetes. As a result, the failure of an individual afflicted with diabetes reliably to monitor their glucose levels is a significant public health problem.

In order to provide an alternative to the existing invasive blood glucose monitoring techniques, non-invasive blood glucose detection techniques have been proposed. One such technique is the non-invasive continuous spectrum infrared spectroscopic technique. One example of such a technique is given in U.S. Pat. No. 5,070,874 (Barnes, et al.) In this technique, a portion of the patient's body is non-invasively irradiated with infrared radiation across a continuous spectrum. Radiation emitted from the body part, which radiation has been either transflected or transmitted, is then detected, to obtain signals representing the intensity of radiation at numerous wavelength ranges within the continuous spectrum. The signals are then processed to obtain an absorbance spectrum. Appropriate analytical techniques are applied to the detected absorbance spectrum in order to obtain a blood glucose level. Concentrations of other blood analytes may also be measured in this manner.

No device using the non-invasive infrared technique has achieved accuracy sufficient to match that of existing invasive techniques. A significant difficulty in obtaining sufficient accuracy is a low signal-to-noise ratio. Continuous-spectrum noninvasive techniques make use of radiation in the near-infrared portion of the spectrum. However, in this portion of the spectrum, the absorption of radiation by water is very high. In addition, the concentrations of the analyte of interest in the bloodstream is typically low. As a result, the contribution of the analyte of interest to the signal intensity is only a relatively small change in the total signal intensity obtained by this technique. It has been found that detector noise is of the same order of magnitude as the change in intensity signal resulting from variations in analyte concentration. The variations in signal intensity as a result of variations in concentration of the analyte of interest are so small that, at intensities that have been used in the past, the detector's sensitivity may not be high enough to obtain sufficiently accurate readings.

A possible solution to this problem would be to increase the intensity of the radiation incident on the body part of the subject. However, an increase in the intensity of incident radiation increases the amount of energy absorbed by the body part. Increases in the energy absorbed by the body part result in greater heating of the body part the amount of heat produced. Excessive heating can cause discomfort and even burns to the subject, which obviously would be undesirable.

It is accordingly an object of this invention to provide a method for the continuous spectrum non-invasive spectroscopic detection of analytes in the bloodstream of living animals with increased signal-to-noise ratio.

Further objects and advantages of the invention will become apparent from the detailed description of a preferred embodiment which follows.

SUMMARY OF THE INVENTION

A method for non-invasive detection of the concentration of an analyte in the blood of a living animal includes the steps of irradiating a body part of the animal with intensity-modulated radiation over a continuous spectrum; detecting the intensity of radiation emitted from the body part at a plurality of discrete wavelength ranges within the continuous spectrum; and using the detected intensity to calculate the concentration of the blood analyte.

An apparatus for non-invasive detection of the concentrations of an analyte in the bloodstream of a living animal includes a source of intensity-modulated radiation over a continuous spectrum for irradiating a body part of the animal; detectors for detecting the intensity of radiation emitted by the body part at wavelength ranges within the continuous spectrum and providing an output signal representative of the detected radiation intensity; and an apparatus for calculating the concentration of the analyte from the detected intensity.

DETAILED DESCRIPTION OF A PREFERRED EMBODIMENT

Figure 1:
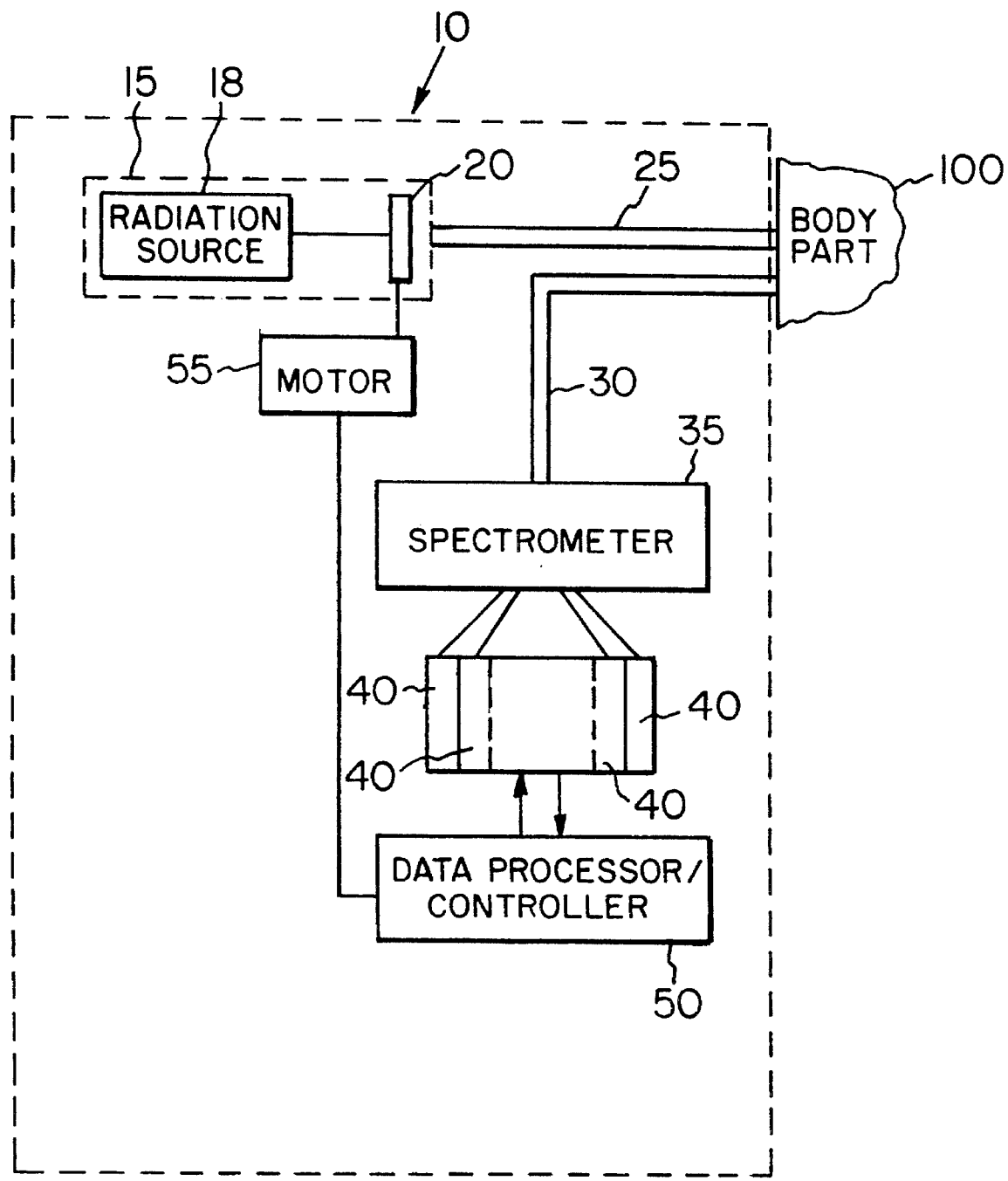
FIG. 1 is a schematic representation of an apparatus for non-invasive detection of analyte concentration in the blood.

Referring to FIG. 1, there is shown, schematically, an apparatus 10 for non-invasively detecting the concentration of an analyte in the bloodstream of an animal. Apparatus 10 includes radiation source 15 which emits intensity-modulated radiation over a continuous spectrum into an input end of incident optical fiber, or bundle of optical fibers 25. An output end of optical fiber bundle 25 is coupled to body part 100. Radiation source 15 preferably alternately repeatedly irradiates body part 100 for a selected interval and does not emit radiation for the selected interval. Radiation source 15 includes a continuously-emitting radiation generator 18, which is preferably a tungsten filament bulb. The temperature of the bulb and current provided to the filament of the tungsten filament bulb are preferably carefully controlled to obtain a constant radiation spectrum. Radiation source 15 also includes chopper 20. Chopper 20 is interposed between radiation generator 18 and body part 100, and preferably between radiation generator 18 and incident optical fiber bundle 25. Chopper 20 alternately interrupts and non-interrupts radiation emitted by radiation generator 18, thereby causing radiation emitted by radiation source 15 to be intensity-modulated, with the intensity vs. time having a square-wave pattern. Chopper 20 is preferably an arm on a pivot. Chopper 20 may also be a selected chopper wheel, such as is known in the art.

A source that provides radiation over a continuous spectrum provides radiation at every wavelength within a range, or at a large number of closely-spaced discrete wavelengths within a range. For example, to provide radiation over a continuous spectrum, at every wavelength within the range from 1100 to 2500 nanometers, a tungsten filament bulb may be used. Alternatively, there could be provided a large number of discrete wavelength radiation sources emitting simultaneously and separated in wavelength, preferably equally, across the spectrum. For example, there could be provided discrete wavelength radiation sources at intervals of about 10–15 nm, to provide radiation over a continuous spectrum.

Chopper 20 is driven by motor 55. Motor 55 is controlled by data processor/controller 50. Motor 55 drives chopper 20 to interrupt radiation from radiation generator 18 at a constant frequency. The frequency may be from about 250 Hz to about 1000 Hz, and in a preferred embodiment, the frequency is about 500 Hertz. The selected interval for which radiation source 15 alternately irradiates body part 100 and does not emit radiation is thus between about 1/500 seconds and 1/2000 seconds, and preferably about 1/1000 seconds. However, the frequency may be selected by those of skill in the art as desired. In the embodiment where chopper 20 is a motor-driven arm, motor 55 is preferably a synchronous, fixed frequency motor.

A portion of the radiation transmitted by incident optical fiber bundle 25 into body part 100 is emitted by body part 100 into pick up optical fiber, or bundle of optical fibers, 30. Pick up optical fiber bundle 30 transmits radiation emitted from body part 100 to spectrometer 35. Spectrometer 35 spectrally separates the radiation, and focuses the radiation on detectors 40. Spectrometer 35 may be, for example, a unitary block of appropriate glass in a Czerny-Turner configuration. Detectors 40 may be, as is conventional in infrared and near-infrared detection, lead-sulfide detectors. A selected wavelength range within the continuous spectrum is focused by spectrometer 35 on each of detectors 40. For example, detectors 40 may be 64 individual detectors, each covering a wavelength range of about 15 nanometers. Each one of detectors 40 produces an output electrical signal whose intensity represents the intensity of the detected radiation. Output electrical signals from detectors 40 are transmitted to pre-amplifier 45. The portion of the signal representing radiation emitted from body part 100 has a known frequency as a result of pulsed or intensity-modulated radiation employed to irradiate body part 100. At pre-amplifier 45, appropriate electronic signal analytical techniques, particularly lock-in modulation techniques, are employed to isolate the portion of the signal which represents radiation emitted from body part 100. Thus, noise, and in particular detector noise, can be filtered out from the signal. It will be understood that pre-amplifier 45 is controlled by data processor/controller 50. After pre-amplifier 45 has removed at least a portion of the noise, the signal is transmitted to data processor/controller 50. In accordance with conventional data processing techniques, data processor/controller 50 obtains an absorbance spectrum, showing absorbance plotted against wavelength.

Upon obtaining an absorbance spectrum, if calibrating apparatus 10, the next step is to determine the analyte concentration in the blood in accordance with conventional invasive techniques. This step is performed by lancing a body part, such as a finger, to obtain a small quantity of blood, and then analyzing the blood in a high accuracy instrument. For example, in order to obtain the concentration of glucose invasively, an analyzer manufactured by Yellow Spring Instruments may be employed. The calibration of the instrument is preferably carried out by data processor/controller 50 using multivariate analytical techniques, employing as data input the absorbance spectrum obtained from the instrument, and the analyte concentration determined from analysis of the invasively-obtained blood sample.

It is also believed to be advantageous to use two absorbance spectra obtained at two different blood volume to tissue volume ratios. This may be done by taking two readings simultaneously at blood rich and blood poor portions of the skin, such as the inside of the wrist and the upper inside of the forearm, or by taking a first reading in a body part such as the finger or the ear lobe, and a second reading with the body part compressed to reduce the blood volume. In the technique either using two different blood volume to tissue volume ratios, or using only one non-invasive set of readings, the multivariate analytical technique may be the method of partial least squares. Various commercial software packages are available that will perform the computations required for partial least squares analysis. Such software packages include, for example, NSAS by NIR Systems of Silver Spring, Md., and Spectra Calc, Lab-Calc and GRAMS by Galactor Industries of Salem, N.H. Those of skill in the art of performing partial least squares analysis will be able to input properly the absorbance spectrum data and the analyte concentration determined from the invasively-obtained blood samples, in order to obtain a set of factors. The set of factors will, when multiplied by given spectrum, provide the concentration of the desired analyte in the blood.

In using the calibrated instrument to obtain an analyte concentration, data processor/controller 50 will, in accordance with conventional techniques, calculate the concentration of the analyte in blood, using the set of factors calculated during calibration of the instrument as discussed above. The concentration is preferably displayed on a suitable display, and may also be stored in an appropriate memory device. The detection step may employ either readings taken at a single blood volume to tissue volume ratio, or may employ readings taken at two different blood volume to tissue volume ratios.

It will be understood that an advantage of the present invention is the reduction in heating of body part 100 as a result of the irradiation of body part 100 with the continuous-spectrum pulsed radiation. In the illustrated embodiment, this is achieved by the location of chopper 20 intermediate radiation generator 18 and body part 100. By locating chopper 20 intermediate radiation generator 18 and body part 100, rather than, for example, intermediate body part 100 and detectors 40, the time average radiation flux on body part 100 is reduced by one-half. Consequently, the intensity of radiation incident on body part 100 may be increased by 100 percent, with no increase in time-average radiation flux and consequently no increase in heating effect. This increase in the intensity of incident radiation results in an increase in the intensity of radiation emitted from body part 100. As a result, the signal-to-noise ratio is improved.

It will be understood that other techniques may be employed to obtain intensity-modulated incident radiation. For example, a radiation source 15 may be provided which can be continuously flashed to obtain a pulsed signal. However, flashing a tungsten-filament bulb, which is the preferred radiation source in the near-infrared, is not practical.

It will be appreciated that there are considerable variations that can be accomplished in a method and apparatus of the intention without departing from its scope. As a result, although a preferred embodiment of a method and apparatus of the invention have been described above, it is emphasized that the invention is not limited to a preferred embodiment and there exists other alternative embodiments that are fully encompassed within the invention's scope, which is intended to be limited only by the scope of the appended claims.

What is claimed is:

1. A method for non-invasive detection of the concentration of a constituent of blood of a living animal, comprising the steps of:

(a) irradiating a body part of the animal with intensity-modulated radiation over a continuous spectrum;

(b) detecting the intensity of radiation emitted from the body part at a plurality of wavelength ranges within said continuous spectrum; and (c) using said detected intensity to calculate the concentration of the constituent.

2. The method of claim 1, wherein said step (c) comprises using lock-in modulation techniques synchronized with the modulation of said radiation simultaneously in said step (a) to filter out noise.

3. The method of claim 1, wherein said step (a) comprises repeatedly alternately irradiating and not irradiating the body part for a selected interval.

4. The method of claim 3, wherein said selected interval is between about 1/2000 seconds and about 1/500 seconds.

5. The method of claim 1, wherein said step (a) comprises providing a continuously emitting radiation generator and a chopper periodically to interrupt the irradiation of said body part by said radiation.

6. The method of claim 1, herein said step (b) comprises focusing radiation emitted from the body part corresponding to each of said wavelength ranges on one of a plurality of detectors.

7. An apparatus for non-invasive detection of the concentration of an analyte in the bloodstream of a living animal, comprising:

(a) a source of intensity-modulated radiation over a continuous spectrum for irradiating a body part of the animal simultaneously over the continuous spectrum;

(b) a plurality of detectors for detecting the intensity of radiation emitted by the body part at a plurality of wavelength ranges within said continuous spectrum and providing an output signal representative of the detected radiation intensity; and (c) means for calculating the concentration of the analyte from said detected intensity.

8. The apparatus of claim 7, further comprising a preamplifier, for receiving said detector output signal and using lock-in modulation techniques synchronized with modulation of said radiation, to isolate the portion of said detector output signal which represents the radiation emitted from the body part.

9. The apparatus of claim 8, wherein said source comprises a continuously-emitting lamp and a chopper positioned intermediate said lamp and the body part to periodically interrupt the irradiation of said body part.

10. The apparatus of claim 7, wherein said radiation source alternately repeatedly emits radiation for a selected interval and non-emits for the selected interval.

11. The apparatus of claim 9, wherein said selected interval is between about 1/500 seconds and 1/2000 seconds.

12. The apparatus of claim 7, further comprising means for focusing radiation emitted from the body part at each of said wavelength ranges on one of said detectors.

13. The apparatus of claim 12, wherein said focusing means comprises a spectrometer.

* * * * *

UNITED STATES PATENT AND TRADEMARK OFFICE
CERTIFICATE OF CORRECTION

PATENT NO. : 5,460,177
DATED : October 24, 1995
INVENTOR(S) : David L. Purdy, Perry Palumbo and Mark DiFrancesco It is certified that error appears in the above-indentified patent and that said Letters Patent is hereby corrected as shown below:

Column 2 Line 18 after "part" insert --and--.

Column 5 Line 16 "intention" should read --invention--.

Claim 4 Line 44 Column 5 "between about 1/2000 seconds and about 1/500 seconds." should read --between about 1/500 seconds and about 1/2000 seconds.--.

Claim 6 Line 5 Column 6 "herein" should read --wherein--.

Claim 11 Line 36 Column 6 "claim 9," should read --claim 10,--.

Signed and Sealed this

Eleventh Day of June, 1996

BRUCE LEHMAN

*Attest:*

*Attesting Officer*  *Commissioner of Patents and Trademarks*